United States Patent
Dileo

[11] Patent Number: 5,921,999
[45] Date of Patent: Jul. 13, 1999

[54] SYSTEM AND METHOD EMPLOYING A PIEZOELECTRIC CRYSTAL AND TRANSVERSE OSCILLATION TO PERFORM A CAPSULOTOMY

[76] Inventor: Frank Dileo, P.O. Box 1668, Bridgehampton, N.Y. 11932

[21] Appl. No.: 08/867,884

[22] Filed: Jun. 3, 1997

Related U.S. Application Data

[51] Int. Cl.⁶ .................................................. A61F 9/00
[52] U.S. Cl. ......................... 606/166; 606/37; 606/39; 606/40; 604/19; 604/22
[58] Field of Search ................................ 606/166, 37, 39, 606/40, 59; 604/19–22

[56] References Cited

U.S. PATENT DOCUMENTS

| | | | |
|---|---|---|---|
| 3,589,363 | 6/1971 | Banko | 604/22 |
| 3,902,495 | 9/1975 | Weiss et al. | 604/22 |
| 4,570,632 | 2/1986 | Woods | 606/166 |
| 4,689,040 | 8/1987 | Thompson . | |
| 4,911,161 | 3/1990 | Schechter . | |
| 5,188,589 | 2/1993 | Wypych et al. | 604/22 |
| 5,279,542 | 1/1994 | Wilk | 604/19 |
| 5,346,491 | 9/1994 | Oertli . | |
| 5,411,511 | 5/1995 | Hall | 606/166 |
| 5,413,556 | 5/1995 | Whittingham . | |
| 5,453,087 | 9/1995 | Malinowski . | |
| 5,507,738 | 4/1996 | Ciervo . | |
| 5,545,172 | 8/1996 | Knepshield et al. | 606/166 |
| 5,634,918 | 6/1997 | Richards | 606/166 |

OTHER PUBLICATIONS

Declaration of Frank Dileo, signed Dec. 14, 1998.

*Primary Examiner*—Michael Buiz
*Assistant Examiner*—Lien Ngo
*Attorney, Agent, or Firm*—Selzman & Levy

[57] ABSTRACT

A system and method for performing a capsulotomy employ a handpiece including a cutting assembly that fits into the anterior chamber of the eye, and cuts an opening in the capsule of the eye with mechanical oscillation. The cutting assembly includes a rigid sleeve enclosing an oscillating shaft. The sleeve and oscillating shaft are configured to induce a laminar flow of fluid in the interior of the sleeve during operation of the system. The cutting member oscillates in a direction transverse to the longitudinal dimension of the handpiece.

16 Claims, 10 Drawing Sheets

SYSTEM AND METHOD EMPLOYING A PIEZOELECTRIC CRYSTAL AND TRANSVERSE OSCILLATION TO PERFORM A CAPSULOTOMY

BACKGROUND OF THE INVENTION

1. Field of the Invention

This invention relates generally to cataract surgery and, more particularly, to that phase of cataract surgery known as an anterior capsulotomy.

2. Description of Related Art

The human eye includes a lens enclosed by a transparent capsule. Cataracts is a condition characterized by opacity of the lens causing partial or total blindness. Cataracts may be relieved with surgery involving removal of the defective lens and replacement with an artificial lens. An initial phase of cataract surgery is an anterior capsulotomy, wherein an opening is made in the capsule to allow the removal of the defective lens.

A known method of performing a capsulotomy is to rupture the capsule with a needle, to create a tear. The surgeon then grasps the free edge of the tear with forceps and maneuvers, by manual dexterity, to create an approximately circular opening in the center of the capsule. Performing a capsulotomy with needle and forceps is difficult and the results are neither uniform nor predictable. This nonuniformity of result is a disadvantage, because the success of the capsulotomy dictates to a large extent the quality and success of the entire cataract operation.

SUMMARY OF THE INVENTION

It is an object of the present invention to provide a system for performing a capsulotomy to achieve relatively uniform results.

To achieve this and other objects of the present invention, a system for performing a capsulotomy under control of a surgeon, comprises a manual control, responsive to manipulation by the surgeon, for generating a first electrical signal; circuitry for generating a second signal in response to the first signal; a handpiece housing defining a longitudinal dimension; an oscillating mechanism, in the handpiece housing, configured to move in response to the second electrical signal; and a cutting member, coupled to the oscillating member, configured to oscillate transverse to the longitudinal dimension.

According to another aspect of the present invention, a method of transforming a system for performing a capsulotomy under control of a surgeon, the system including a manual control, responsive to manipulation by the surgeon, for generating a first electrical signal; circuitry for generating a second signal in response to the first signal; a handpiece housing defining a longitudinal dimension; an oscillating mechanism, in the handpiece housing, configured to move in response to the second electrical signal; an aspirator; a first cutting member defining a pointed distal end; and a second cutting member defining a hollow distal end, comprises the steps of coupling the first cutting member to the oscillating member; activating the manual control to cause the first cutting member to oscillate transverse to the longitudinal dimension; removing the first cutting member from the oscillating member; coupling the second cutting member to the oscillating member, such that the hollow end is in fluid communication with the aspirator; activating the aspirator to induce a fluid flow into the hollow end; and activating the manual control to cause the second cutting member to oscillate.

The accompanying drawings which are incorporated in and which constitute a part of this specification, illustrate embodiments of the invention and, together with the description, explain the principles of the invention, and additional advantages thereof. Throughout the drawings, corresponding parts are labeled with corresponding reference numbers.

DESCRIPTION OF THE PREFERRED EMBODIMENT

Figure 1:
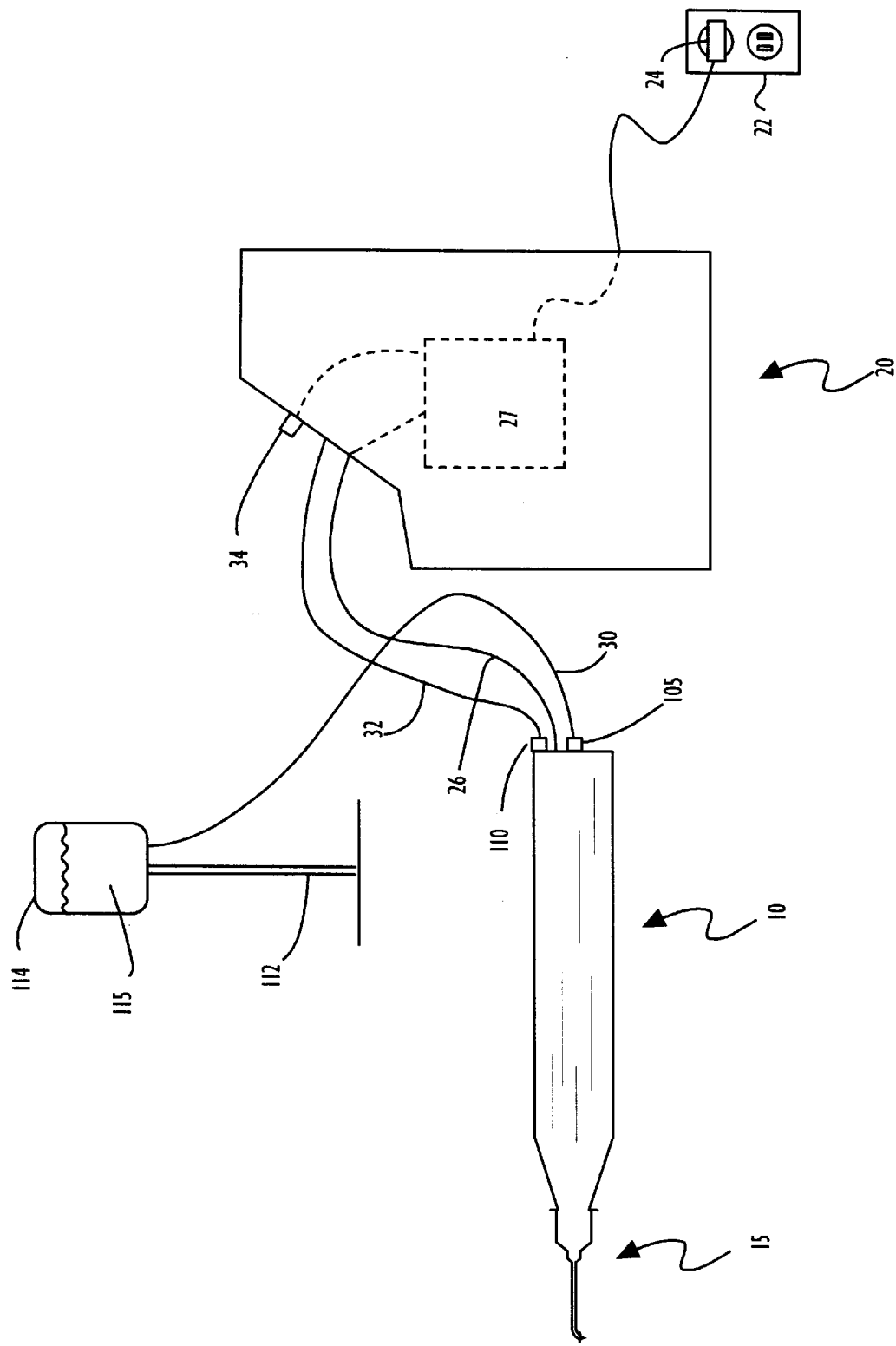
FIG. 1 is a diagram of a system configured to perform a capsulotomy according to a preferred embodiment of the invention.

FIG. 1 shows a capsulotomy system according to the preferred embodiment of the invention. Handpiece 10 includes cutting assembly 15 for cutting an opening in the capsule of the eye with mechanical oscillation. Handpiece 10 is approximately 5 to 6 inches in length.

Handpiece 10 includes connector 105 for removably connecting a fluid conduit, such as fluid conduit 30. Handpiece 10 also includes connector 110 for removably connecting a fluid conduit, such as fluid conduit 32.

Kiosk 20, which is not depicted to scale, is approximately three and one-half feet in height. Kiosk 20 supplies an AC signal of ultrasonic frequency to handpiece 10, via electrical cable 26. Kiosk 20 supplies a vacuum to handpiece 10, via fluid conduit 32.

Circuitry 27 in kiosk 20 receives power from 60 Hz outlet 22 via plug 24. Circuitry 27 is responsive to manual on-off switch 34, and supplies the ultrasonic AC signal on cable 26 responsive to activation of switch 34.

Irrigation bag 114 is supported above handpiece 10 by stand 112. Bag 114 includes sterile irrigation solution 115. Bag 114 supplies irrigation fluid 115 to handpiece 10, via conduit 30.

It is presently preferred that handpiece 10 include all the structure of a known ultrasonic handpiece for performing the phacoemulsification phase of cataract surgery. Such a handpiece is described, for example, in U.S. Pat. No. 5,453,087 to Malinowski, filed Nov. 26, 1993 and issued Sep. 26, 1995, the contents of which is herein incorporated by reference. It is also preferred that kiosk 20 include all the structure of a known power unit for operating such a phacoemulsification handpiece. Because phacoemulsification handpieces and power units are known in the art, the description of the internal structures of hand piece 10 and kiosk 20 is highly simplified in this patent application.

Figure 2A:
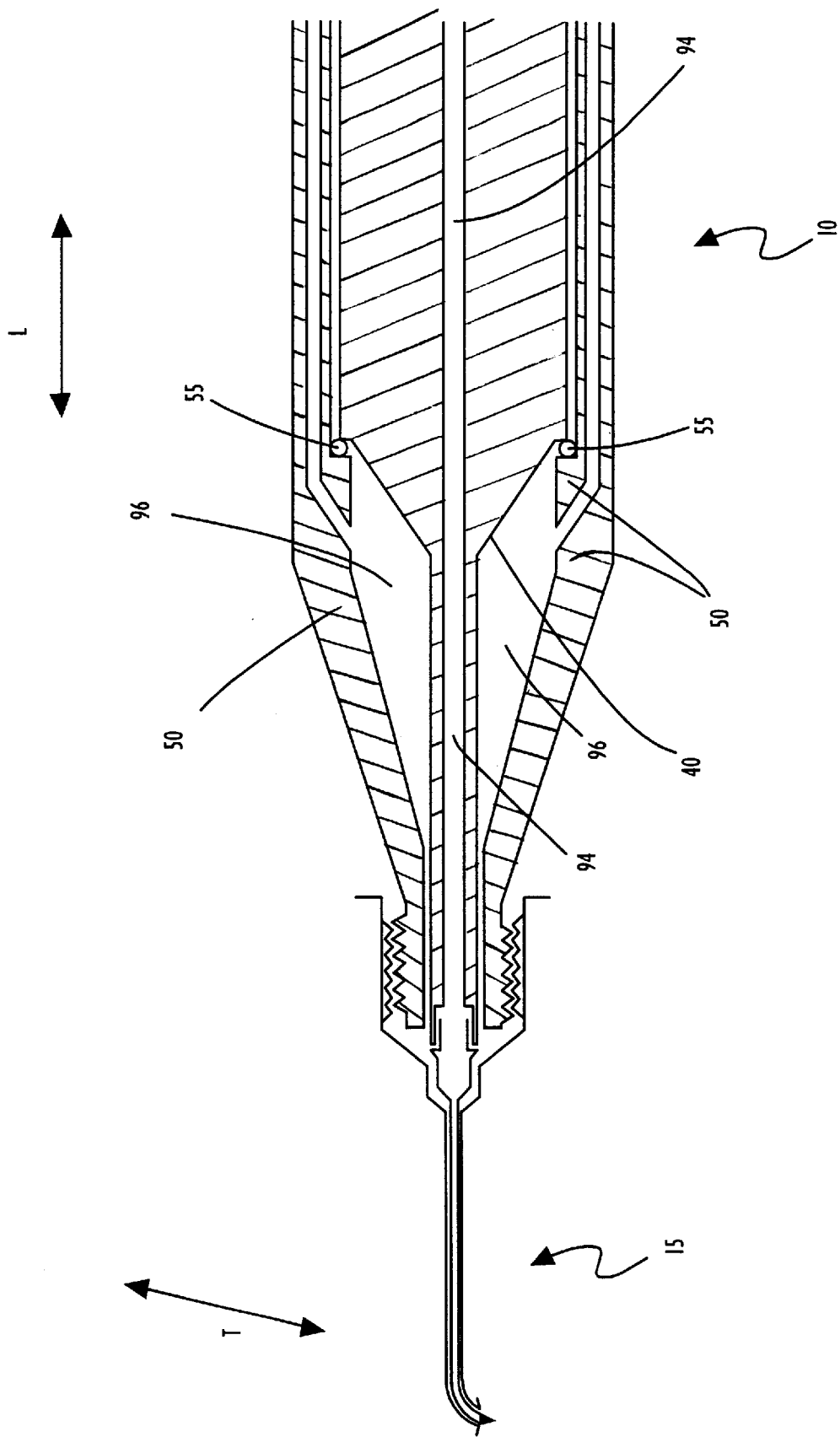
FIG. 2A is a simplified cross-section of the front part of the handpiece shown in FIG. 1.
Figure 2B:
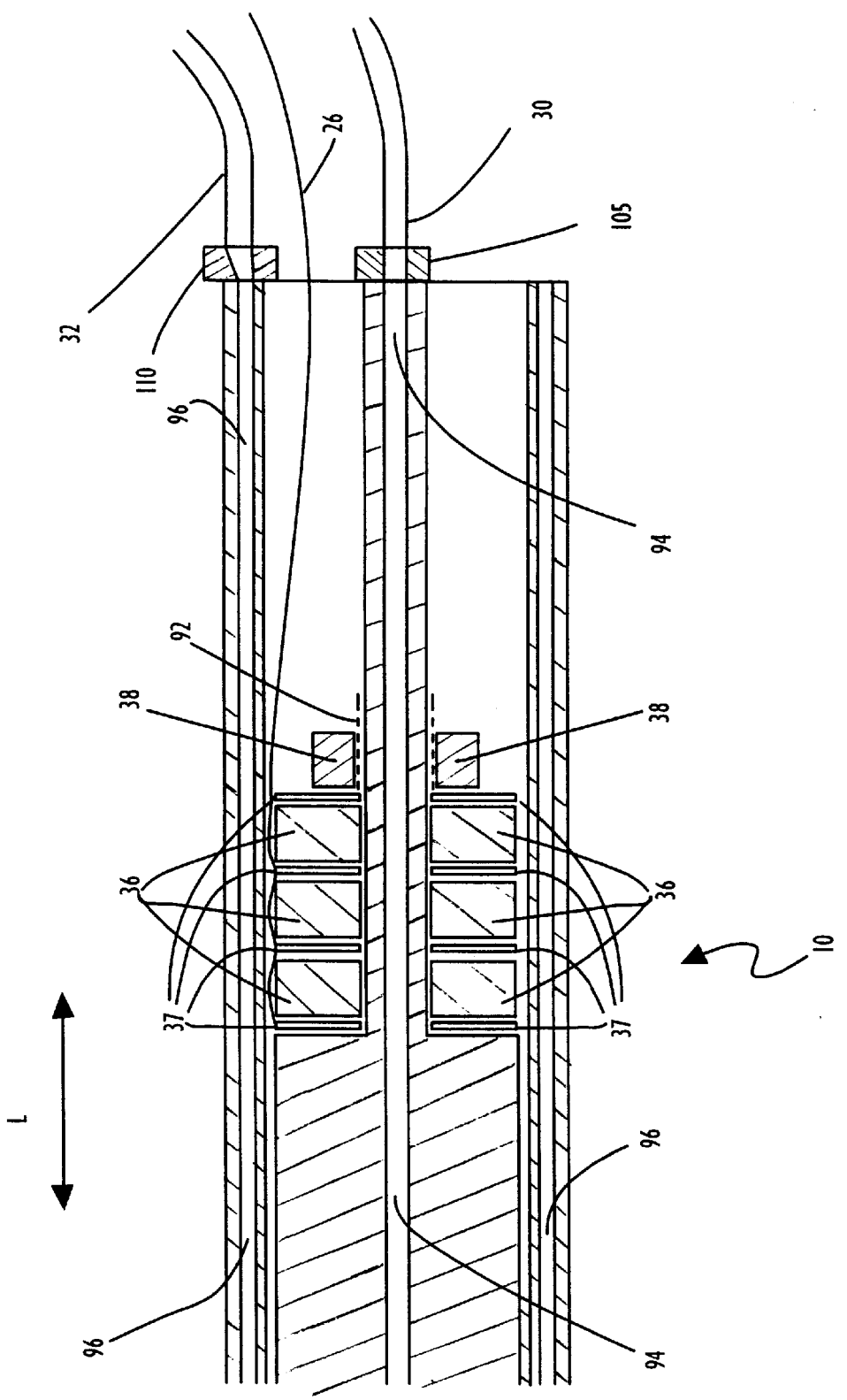
FIG. 2B is a simplified cross-section of the back part of the handpiece shown in FIG. 1.

FIG. 2A is a highly simplified cross-section of the front part of handpiece 10 shown in FIG. 1, and FIG. 2B is a highly simplified cross-section of the back part of handpiece 10. Handpiece 10 includes shell 50 enclosing horn 40. O-ring 55 and other O-rings (not shown) are positioned to mechanically isolate shell 50 from horn 40. Horn 40 has a shaft portion 41 that defines threads 92. Nut 38 engages threads 92 on shaft 41 to apply pressure to piezo electric crystals 36 and secure piezo electric crystals to horn 40. Multiwire electric cable 26 applies the AC ultrasonic signal to crystals 36 via electrodes 37, thereby causing crystals 36 to mechanically oscillate. The oscillation of crystals 36 cause horn 40 to oscillate along the longitudinal dimension of handpiece 10, the direction of the line L.

As shown in FIGS. 2A and 2B, horn 40 defines a central fluid channel 94. Fluid channel 94 is in fluid communication with connector 105 and external fluid conduit 30. Shell 50 defines an outer fluid channel 96. Fluid channel 96 is in fluid communication with connector 110 and external conduit 32. Channel 96 in concentrically arranged around channel 94.

Figure 3:
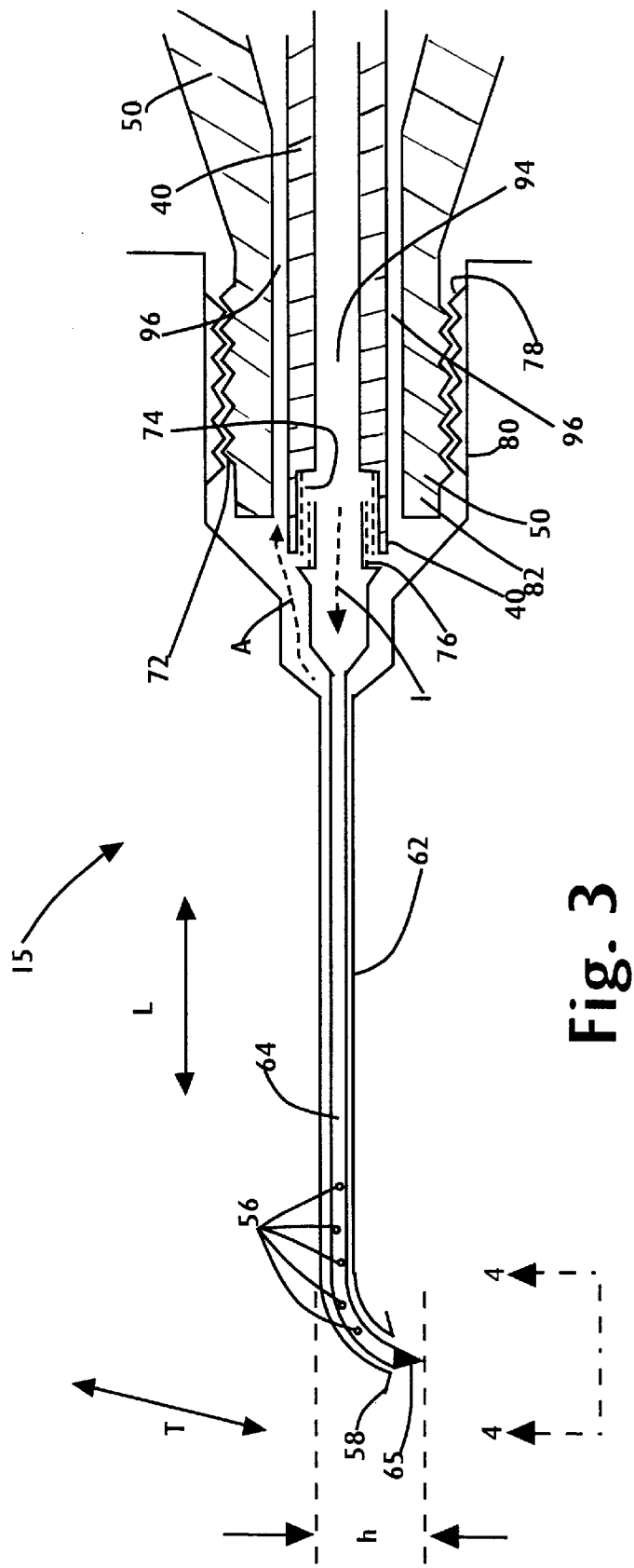
FIG. 3 is an enlarged cross-section of a portion of the system shown in FIG. 2.

FIG. 3 shows an enlarged view of cutting assembly 15 including rigid sleeve 62 enclosing oscillating shaft 64. Oscillating shaft 64 includes a hollow portion defining fluid holes 56 for inducing a laminar flow of fluid in the interior sleeve 62 during operation of the system to perform the capsulotomy. Oscillating shaft 64 includes external threads 74 having the same pitch as the threads of a conventional phacoemulsification needle. Shaft 64 is removably attached to horn 40 via exterior threads 76 on shaft 64 and internal threads 74 in the central fluid channel of horn 40.

Sleeve 62 is removably attached to shell 50, via grooves 78 on sleeve base 80 and grooves 72 on shell 50. Grooves 78 and 72 make a fluid tight seal that prevents fluids, in channels 94 and 96, from leaking out of handpiece 10.

Shaft 64 oscillates longitudinally relative to sleeve 62, because O-ring 55 (FIG. 2A) and other O-rings (not shown) act to mechanically decouple horn 40 from shell 50. These longitudinal vibrations cause tip 65 of cutting member 15 to oscillate in a direction transverse to the longitudinal dimension, along the line T, because sleeve 62 defines a downwardly curved distal end, and shaft 64 defines a curved part enclosed by the curved distal end of sleeve 62. The curved part of shaft 64 is flexible relative to sleeve 62. Thus, sleeve 62 acts to guide oscillating shaft 64 so that rigid, sharp end 65 of oscillating shaft 64 oscillates in a direction transverse to the longitudinal dimension of handpiece 10, the direction of the line T. While the curved part of sleeve 62 guides oscillating shaft 64, the laminar fluid flow induced by fluid from holes 56 acts to lubricate the interface between sleeve 62 and shaft 64.

Flange 58, attached to the end of sleeve 62 and extending away from sleeve 62, contacts the capsule and therefore acts to stabilize the capsule allowing sharp tip 65 to move relative to the capsule. Thus, sharp end 65 acts to cut the capsule with and up and down oscillating motion.

Cutting assembly 15 should define a height (h) of no more than 3 millimeters to ensure that cutting assembly 15 fits into the anterior chamber of the eye.

Figure 4:
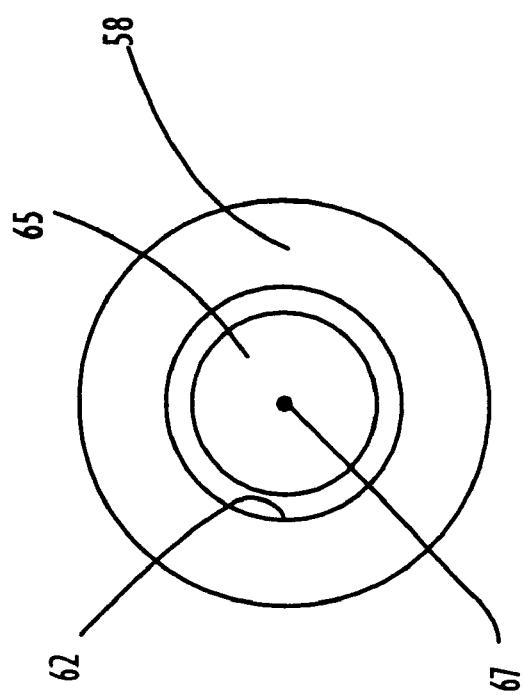
FIG. 4 is a view of the preferred capsulotomy system, taken along the line A—A in FIG. 3.

FIG. 4 is a bottom view taken along the line A—A of FIG. 3. Stabilizing flange 58 extends away from sleeve 62. Sharp tip 65 defines a point 67. From the perspective of FIG. 4, flange 58 defines an outer diameter of approximately 2 millimeters and shaft 65 defines an outer diameter of approximately 1 millimeter.

To assemble the preferred capsulotomy system, the surgeon screws the exterior threads 76 of oscillating shaft 64 into the interior threads 74 of horn 40. Then, the surgeon places base part 80 on end portion 82, to engage grooves 78 of base part 80 with grooves 72 of end portion 82. Because the resilient, silicone inner diameter of base part 80 is normally slightly less than the outer diameter of end portion 82 of horn 50, grooves 78 and grooves 72 make a fluid tight seal.

Figure 5:
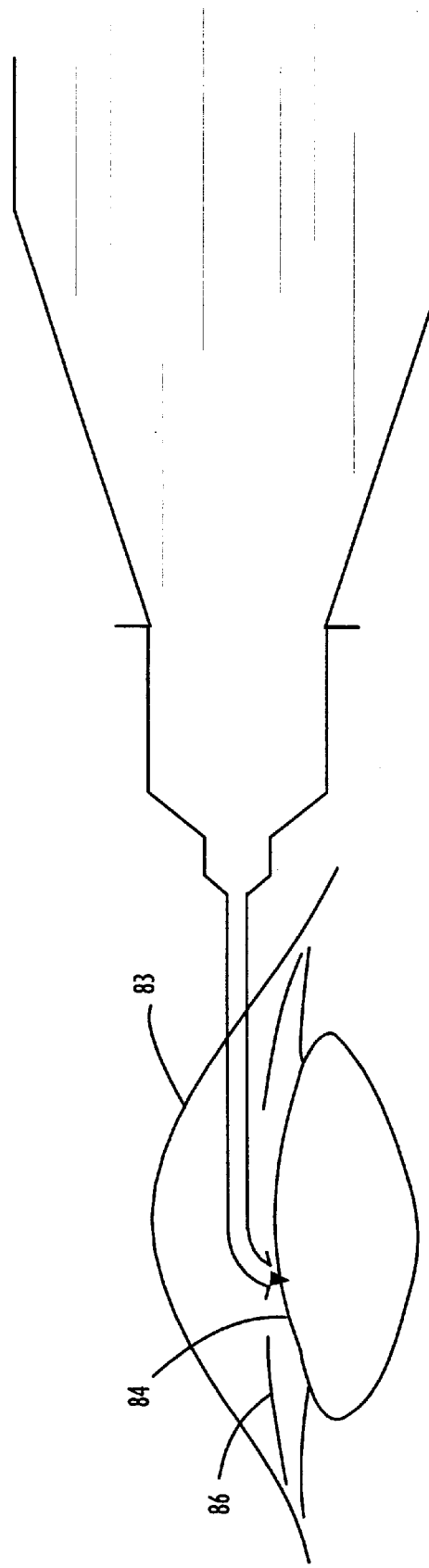
FIG. 5 is a side view showing the preferred capsulotomy system cutting the interior portion of a capsule.

FIG. 5 is a simplified diagram of handpiece 10 and the eye, including capsule 84, iris 86, and cornea 83, during the capsulotomy phase of the surgery. As shown is FIG. 3, during the capsulotomy phase fluid from fluid conduit 30 (FIG. 2B) flows in the direction of the arrow I through holes 56 in oscillating shaft 64. The fluid then travels back through the interior of sleeve 62 into channel 96 as shown by the arrow A, and exits from the handpiece via fluid conduit 32.

Figure 6:
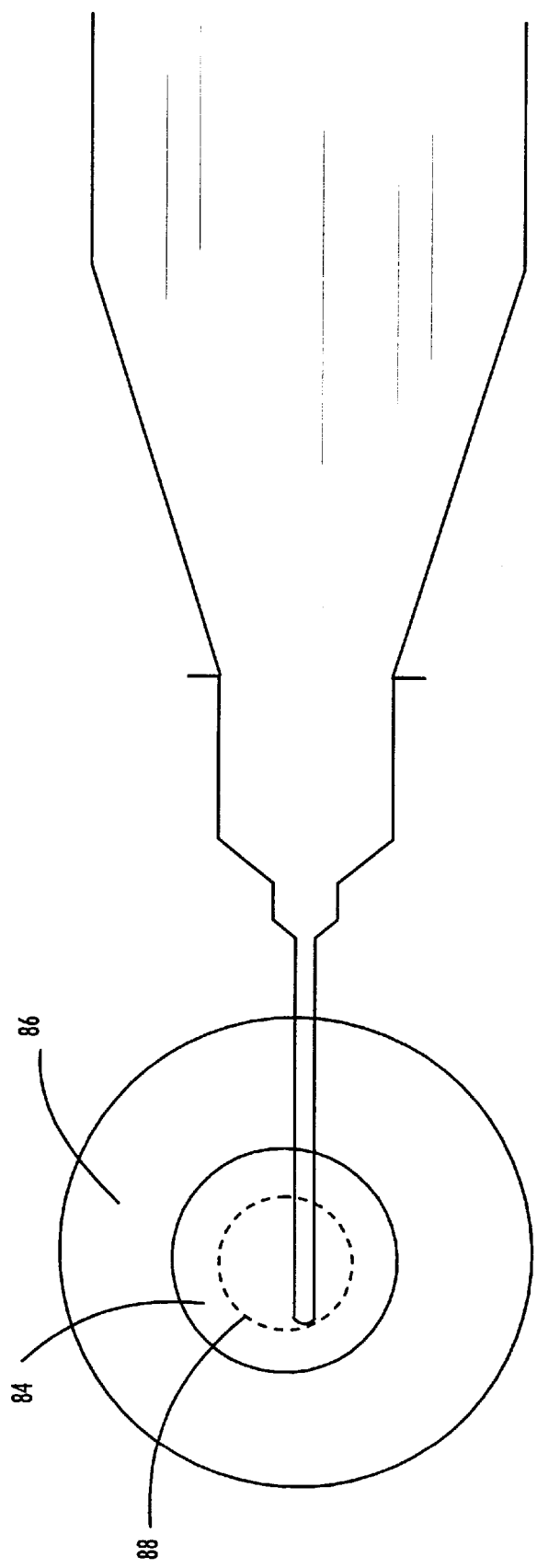
FIG. 6 is a top view corresponding to the view shown in FIG. 5.

FIG. 6 is a top view corresponding to the view shown in FIG. 5. The surgeon moves the preferred capsulotomy system in a circular motion to make opening 88 in capsule 84.

In summary, the preferred capsulotomy system includes switch 34, which is a manual control responsive to manipulation by the surgeon, for generating a first electrical signal and sending the first signal to circuitry 27. Circuitry 27 includes circuitry for generating a second signal in response to the first signal, and sending the second signal to piezo electric crystals 36 in handpiece 10, via electrical cable 26. During the capsulotomy phase, the surgeon adjust controls on kiosk 10 so that the second signal has approximately 50% of maximum power, causing tip 65 to oscillate with a peak to peak amplitude of approximately 1 millimeter. Circuitry 27 includes circuitry to generate and send an AC signal on cable 26 such that shaft 64 oscillates at greater than 10,000 Hz.

Shell 50 is the housing of handpiece 10. Shell 50 defines a longitudinal dimension. Piezo electric crystal 36 in shell 50 act as an oscillating mechanism configured to move in response to the second signal. Shaft 64, coupled to crystals 36 via horn 40, is configured to oscillate transversely to the longitudinal dimension.

Oscillating shaft 64 acts as a cutting member. Oscillating shaft 64 is inside sleeve 62 and is screwed into horn 40. Sleeve 62 is attached to shell 50. O-ring 55 allows horn 40 to oscillate relative to shell 50. Thus, shaft 64 is configured to move relative to sleeve 62. Sleeve 62 acts to convert the longitudinal oscillations of shaft 64 into transverse oscillation, because sleeve 62 has an end defining a curved path for shaft 64. This curved part of sleeve 62 is rigid relative to the curved part of shaft 64.

Elevated bag 114 is a fluid source. Shaft 64 and sleeve 62 define a channel between shaft 64 and sleeve 62. This channel is in fluid communication with the fluid source via holes 56 in shaft 64 and fluid conduit 30. Holes 56 act to induce a laminar fluid flow in this channel between shaft 64 and sleeve 62.

Kiosk 20 is a vacuum source (an aspirator). The channel between ,haft 64 and sleeve 62 is in fluid communication with the aspirator via aspiration channel 96 in the handpiece and fluid conduit 32.

Flange 58 acts as a stabilizing member for the capsule. Flange 58 is attached to shell 50 via sleeve 62.

Thus, the preferred system allows a surgeon to perform a capsulotomy with relatively uniform results.

Figure 7:
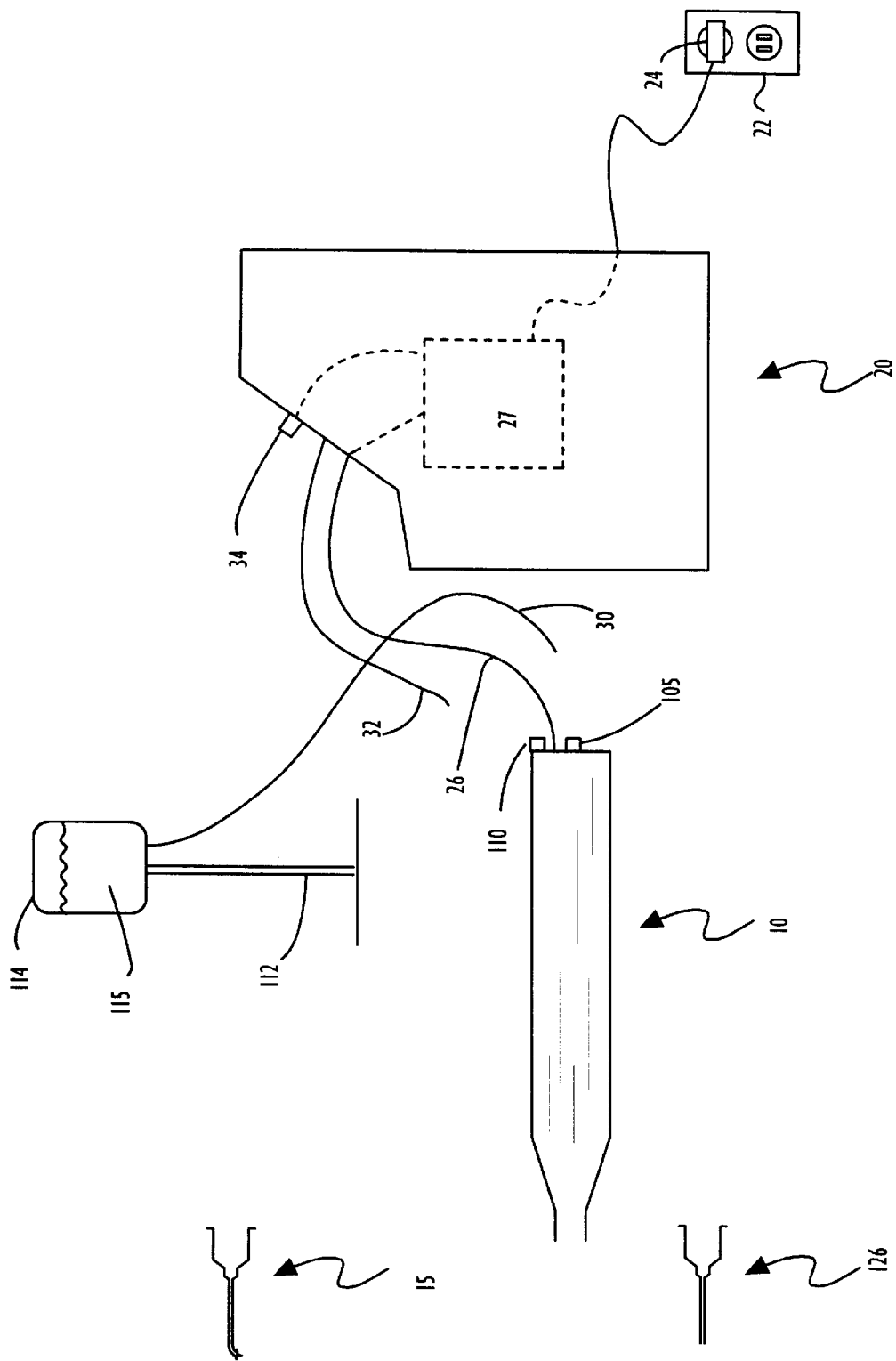
FIG. 7 is a diagram of a system being transformed for the phacoemulsification phase of the cataract surgery.
Figure 8:
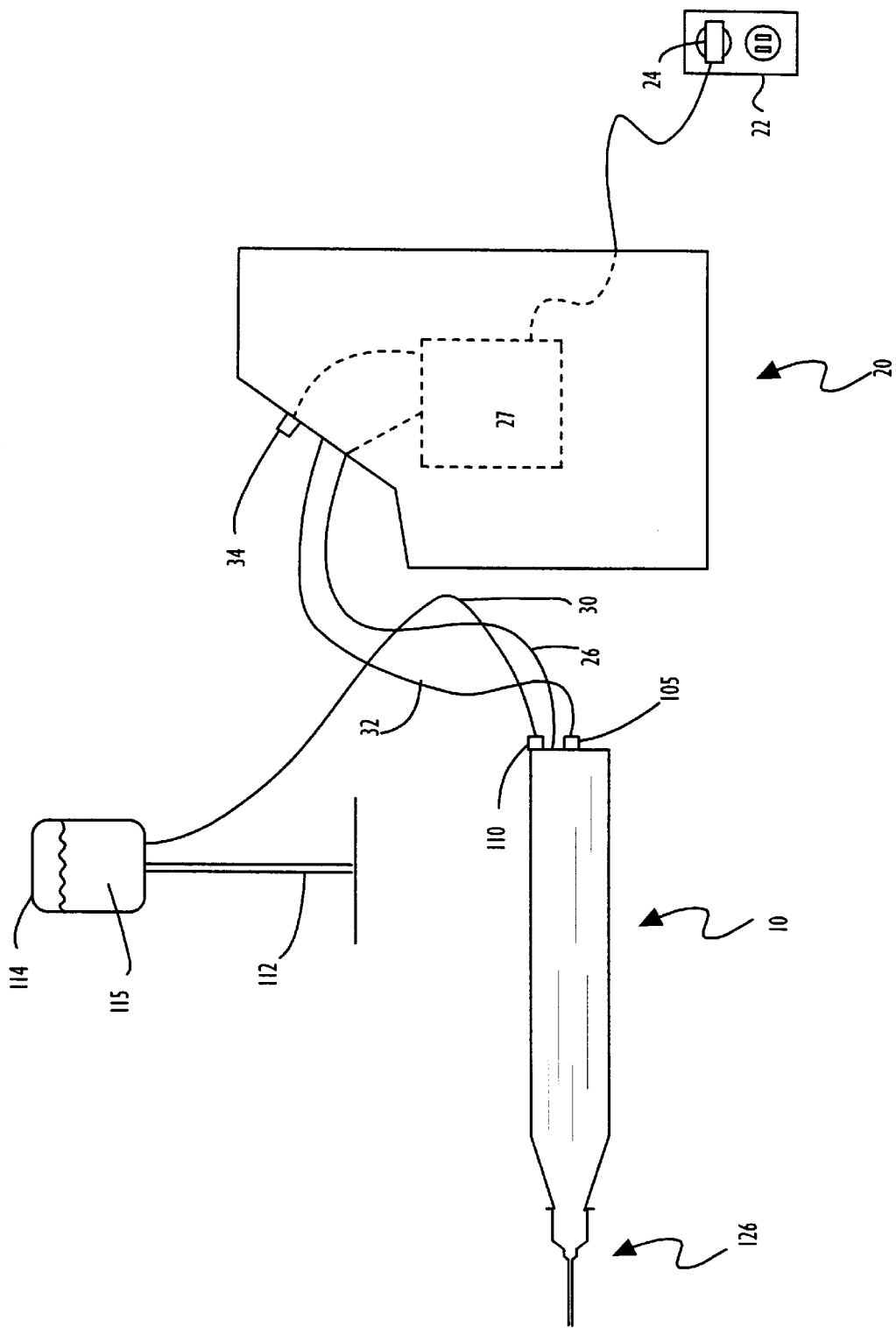
FIG. 8 is a diagram the system configured to perform the phacoemulsification phase of the cataract surgery.

Because handpiece 10 includes all the mechanical structure of a known handpiece for performing the phacoemulsification phase of cataract surgery, and kiosk 20 includes all the circuitry and conduits for operating such a phacoemulsification handpiece, after the capsulotomy phase of the cataract surgery the preferred system may be converted to also perform the phacoemulsification phase of the surgery. As shown in FIGS. 7 and 8, this conversion includes replacing cutting assembly 15 with a phacoemulsification assembly 126 having a hollow end for vacuuming the emulsified lens. The surgeon removes fluid conduit 32 from connector 110 and removes fluid conduit 30 from connector 105, and subsequently attaches conduit 32 to connector 105 and attaches conduit 30 to connector 110. The surgeon adjusts controls (not shown) on kiosk 20 to increase the power of the AC signal to approximately 75%.

Figure 9:
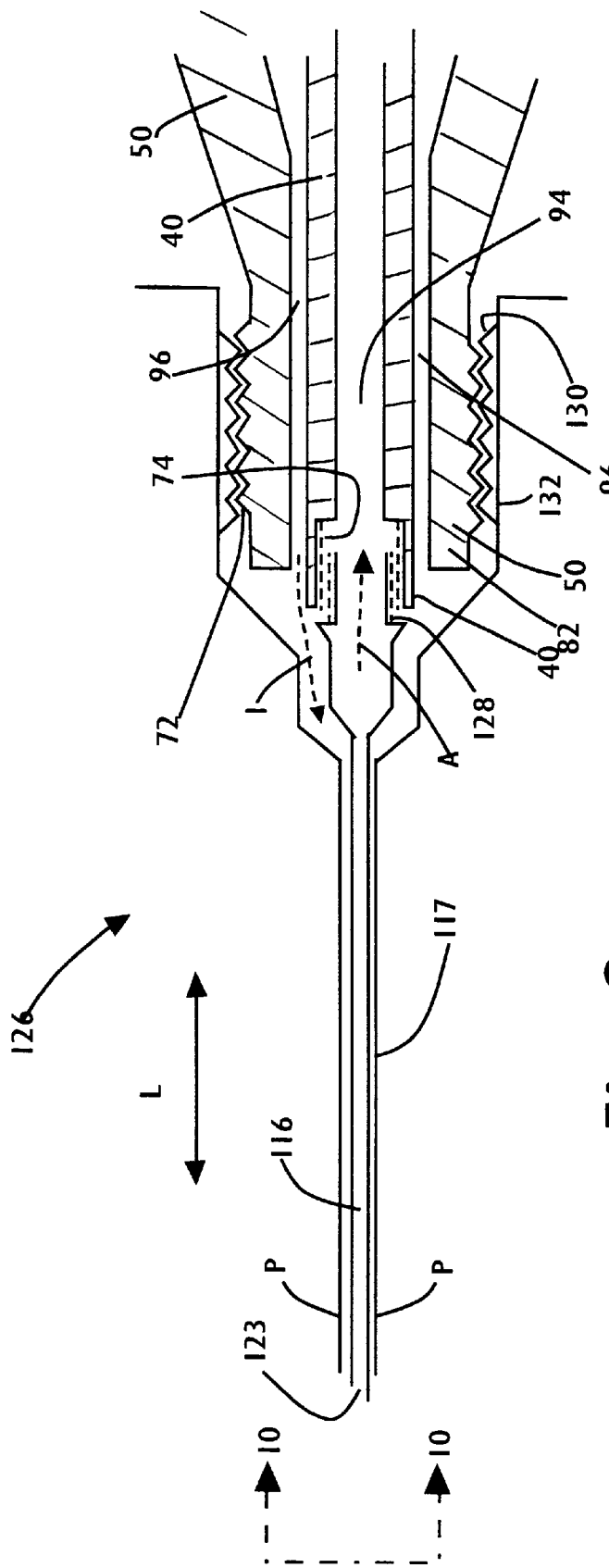
FIG. 9 is an enlarged cross-section of a portion of the system shown in FIG. 8.

FIG. 9 shows an enlarged view of phacoemulsification cutting assembly 126, including resilient silicone sleeve 117 enclosing oscillating shaft 116. Sleeve 117 defines two holes, at locations designated P in FIG. 9, in fluid communication with channel 96. The holes in sleeve 117 introduce fluid into the eye. Metallic oscillating shaft 116 defines a central aspiration channel 116, in fluid communication with channel 94 in horn 10, for vacuuming the emulsified lens out of the eye.

Oscillating shaft 116 includes external threads 128 having the same pitch as threads 74 of horn 40. Shaft 116 is removably attached to horn 40 via exterior threads 128 on shaft 116 and internal threads 74 in the central fluid channel of horn 40. Sleeve 117 is removably attached to shell 50, via grooves 130 on sleeve base 132 and grooves 72 on shell 50. Shaft 116 oscillates relative to sleeve 117, because O-ring 55 and other O-rings (not shown) act to mechanically decouple horn 40 from shell 50. These longitudinal vibrations cause the hollow end of shaft 116 to oscillate in a the longitudinal dimension, along the line L.

Figure 10:
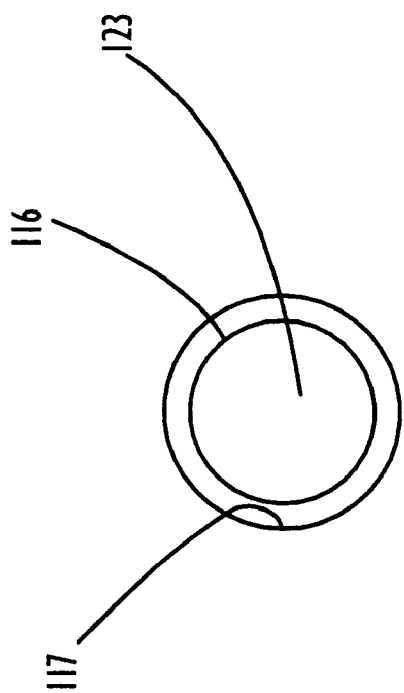
FIG. 10 is a view taken along the line B—B in FIG. 9.

FIG. 10 is a bottom view taken along the line B—B of FIG. 9. Phacoemulsification needle 116 defines a central channel 123 in fluid communication with channel 94 in horn 10.

To configure the system for phacoemulsification, the surgeon screws the exterior threads 128 of needle 116 into the interior threads 74 of horn 40. Then, the surgeon places base part 132 on end portion 82, to engage grooves 132 of base part 80 with grooves 72 of end portion 82. Because base part 132 of sleeve 117 is a resilient silicone compound, and the inner diameter of base part 132 is normally slightly less than the outer diameter of end portion 82 of horn 50, grooves 132 and grooves 72 make a fluid tight seal.

Thus, the surgeon couples cutting assembly 15 (a first cutting member) to horn 40 (an oscillating member), and activates manual control 34 to cause cutting member 15 to oscillate transversely to the longitudinal dimension of handpiece 10. The surgeon then removes cutting member 15 from horn 40 and couples phacoemulsification assembly 126 (a second cutting member) to horn 40 such that the hollow end 123 of phacoemulsification needle 116 is in fluid communication with the vacuum source of kiosk 20, via fluid conduit 32. The surgeon the reactivates manual control 34 to cause phacoemulsification needle 116 to oscillate in the longitudinal direction of handpiece 10, and activates the aspirator to induce a fluid flow into hollow end 123.

Although the illustrative system includes a kiosk for powering a handpiece and supplying fluid to the handpiece, the invention in its broadest sense is not so limited. For example, a standalone, battery operated, handpiece might be employed to cut the capsule with an oscillating motion.

Additional advantages and modifications will readily occur to those skilled in the art. The invention in its broader aspects is therefore not limited to the specific details, representative apparatus, and illustrative examples shown and described. Accordingly, departures may be made from such details without departing from the spirit or the scope of Applicants' general inventive concept. The invention is defined in the following claims.

What is claimed is:

1. A system for performing a capsulotomy under control of a surgeon, the system comprising:
   a manual control, responsive to manipulation by the surgeon, for generating a first electrical signal;
   circuitry for generating a second electrical signal in response to the first signal;
   a handpiece housing defining a longitudinal dimension;
   an oscillating mechanism, in the handpiece housing, configured to move in response to the second electrical signal;
   a fluid source;
   a sleeve; and
   a cutting member coupled to the oscillating mechanism, the cutting member in the sleeve such that the sleeve and the cutting member define a channel between the sleeve and the cutting member, the cutting member including a mechanism that causes a laminar fluid flow in the channel whereby the channel is in fluid communication with the fluid source, the cutting member configured to move relative to the sleeve, and configured to oscillate transverse to the longitudinal dimension.

2. The system of claim 1 further including an aspirator, and a tube defining a channel in fluid communication with the aspirator.

3. The system of claim 1 wherein the circuitry includes means for generating the second signal such that the oscillating mechanism oscillates at greater than 10,000 Hz.

4. The system of claim 1 further including a stabilizing member, mechanically coupled to the handpiece housing, for contacting the capsule while the cutting member cuts the capsule.

5. The system of claim 4 wherein the stabilizing member is attached to the sleeve.

6. The system of claim 1 wherein the sleeve defines a curved path for the cutting member.

7. A method of controlling a system for performing a capsulotomy under control of a surgeon, the system including a manual control, responsive to manipulation by the surgeon, for generating a first electrical signal; circuitry for generating a second electrical signal in response to the first signal; a handpiece housing defining a longitudinal dimension; an oscillating mechanism, in the handpiece housing, configured to move in response to the second electrical signal; an aspirator; a fluid source; a sleeve; a first cutting member coupled to the oscillating mechanism, the first cutting member in the sleeve such that the sleeve and the cutting member define a channel between the sleeve and the first cutting member, the first cutting member including a mechanism that causes a first laminar fluid flow in the channel whereby the channel is in fluid communication with the fluid source, the first cutting member configured to move relative to the sleeve; and a second cutting member defining a hollow distal end, the method comprising the steps of:
   coupling the first cutting member to the oscillating member;
   activating the manual control to cause the first cutting member to oscillate transverse to the longitudinal dimension;

removing the first cutting member from the oscillating member;

coupling the second cutting member to the oscillating member, such that the hollow end is in fluid communication with the aspirator;

activating the aspirator to induce a second fluid flow into the hollow end; and activating the manual control to cause the second cutting member to oscillate.

8. The system of claim 1 further including a stabilizing member, fixedly attached relative to the handpiece housing, for contacting the capsule while the cutting member cuts the capsule.

9. A method for a system for performing a capsulotomy under control of a surgeon, the system including a handpiece housing defining a longitudinal dimension, a first member in the handpiece housing, and a fluid source, a sleeve, a first cutting member coupled to the oscillating mechanism, the cutting member in the sleeve such that the sleeve and the cutting member define a channel between the sleeve and the cutting member, the cutting member including a mechanism that causes a laminar fluid flow in the channel whereby the channel is in fluid communication with the fluid source, the cutting member configured to move relative to the sleeve, the method comprising:

coupling the cutting member to the first member;

generating a first electrical signal in response to manipulation by the surgeon;

generating a second electrical signal in response to the first electrical signal;

oscillating the first member in response to the second electrical signal; and oscillating the cutting member, in the eye, transverse to the longitudinal dimension of the handpiece housing.

10. The system of claim 1 wherein the cutting member has an elliptical cross section.

11. The system of claim 1 wherein the cutting member has a circular cross section.

12. The method of claim 9 further including effecting a fluid flow inside the cutting member while generating the second electrical signal.

13. The method of claim 9 further including effecting a fluid flow in a distal end of the cutting member.

14. The system of claim 1 wherein the oscillating mechanism includes a piezoelectric crystal.

15. The method of claim 7 wherein the oscillating member includes a piezoelectric crystal and the step of coupling a first cutting member includes coupling the first cutting member to the piezoelectric crystal.

16. The method of claim 9 wherein the first member includes a piezoelectric crystal and the step of oscillating the first member includes oscillating the piezoelectric crystal.

* * * * *